United States Patent
Ferry et al.

(10) Patent No.: US 10,342,547 B2
(45) Date of Patent: Jul. 9, 2019

(54) GUIDEWIRE/ PARTIAL OCCLUDER FOR INTRALUMINAL TRAVEL

(71) Applicants: Steven J. Ferry, Excelsior, MN (US); DeLois Marlene Ferry, Excelsior, MN (US)

(72) Inventors: Steven J. Ferry, Excelsior, MN (US); DeLois Marlene Ferry, Excelsior, MN (US)

(73) Assignee: NeuroVASx, Inc., Excelsior, MN (US)

( * ) Notice: Subject to any disclaimer, the term of this patent is extended or adjusted under 35 U.S.C. 154(b) by 393 days.

(21) Appl. No.: 14/774,775

(22) PCT Filed: Mar. 10, 2014

(86) PCT No.: PCT/US2014/022730
§ 371 (c)(1),
(2) Date: Sep. 11, 2015

(87) PCT Pub. No.: WO2014/164535
PCT Pub. Date: Oct. 9, 2014

(65) Prior Publication Data
US 2016/0045202 A1    Feb. 18, 2016

Related U.S. Application Data

(60) Provisional application No. 61/776,492, filed on Mar. 11, 2013.

(51) Int. Cl.
*A61B 17/12* (2006.01)
*A61K 31/231* (2006.01)
(Continued)

(52) U.S. Cl.
CPC .... *A61B 17/12136* (2013.01); *A61B 17/1204* (2013.01); *A61B 17/12109* (2013.01);
(Continued)

(58) Field of Classification Search
CPC .......... A61B 17/12136; A61B 17/1204; A61B 17/12109; A61B 2017/12068;
(Continued)

(56) References Cited

U.S. PATENT DOCUMENTS 6,066,157 A    5/2000  Barbere
6,635,068 B1 * 10/2003  Dubrul ............. A61B 17/12022
                                                    606/200

(Continued)

FOREIGN PATENT DOCUMENTS

WO    WO-9908743 A1    2/1999
WO    WO-2014164535 A1  10/2014

OTHER PUBLICATIONS

"Application Serial No. PCT/US2014/022730, International Preliminary Report on Patentability dated Sep. 24, 2015", 15 pgs.

(Continued)

*Primary Examiner* — Christopher L Templeton
*Assistant Examiner* — George J Ulsh
(74) *Attorney, Agent, or Firm* — Schwegman Lundberg & Woessner, P.A.

(57) ABSTRACT

Inventive subject matter disclosed herein includes a device that includes a hollow tube having a tapered distal end, sized to fit within a blood vessel. The device also includes a tether positioned within the hollow tube and an actuator effective for moving the tether forward and backward with respect to the hollow tube. The device also includes a compliant mesh balloon having proximal end and a distal end, wherein the proximal end is attached to the hollow tube and the distal end is affixed to the tether wherein forward movement of the tether by movement of the actuator elongates the mesh balloon for travel through the blood vessel.

6 Claims, 5 Drawing Sheets

(51) Int. Cl.
*A61K 9/16* (2006.01)
*A61K 9/20* (2006.01)
*A61K 31/5377* (2006.01)
*A61J 3/10* (2006.01)
*A61M 25/10* (2013.01)

(52) U.S. Cl.
CPC .............. *A61J 3/10* (2013.01); *A61K 9/1617* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2077* (2013.01); *A61K 9/2095* (2013.01); *A61K 31/231* (2013.01); *A61K 31/5377* (2013.01); *A61M 25/1002* (2013.01); *A61B 2017/12068* (2013.01); *A61B 2017/12086* (2013.01)

(58) Field of Classification Search
CPC ... A61B 2017/12086; A61B 17/12113; A61M 25/1002; A61M 2025/1068
USPC ........................................................ 606/195
See application file for complete search history.

(56) References Cited

U.S. PATENT DOCUMENTS

| | | | |
|---|---|---|---|
| 6,994,717 | B2 | 2/2006 | Kónya et al. |
| 8,029,530 | B2 | 10/2011 | Gesswein et al. |
| 2004/0176797 | A1* | 9/2004 | Opolski ........... A61B 17/12022 606/213 |
| 2012/0022574 | A1 | 1/2012 | Mafi et al. |
| 2012/0330348 | A1 | 12/2012 | Strauss et al. |

OTHER PUBLICATIONS

"International Application Serial No. PCT/US2014/022730, International Search Report dated Jul. 17, 2014", 4 pgs.
"International Application Serial No. PCT/US2014/022730, Written Opinion dated Jul. 17, 2014", 13 pgs.

* cited by examiner

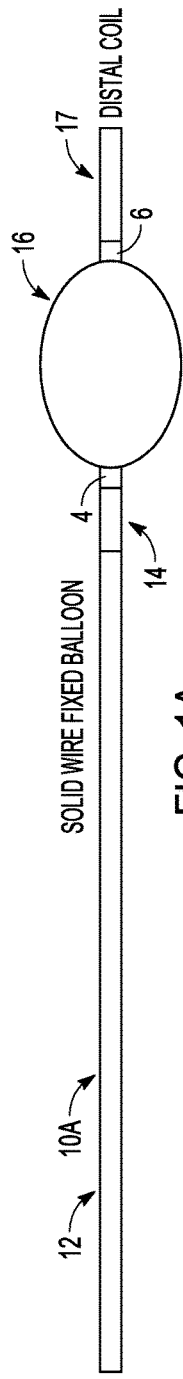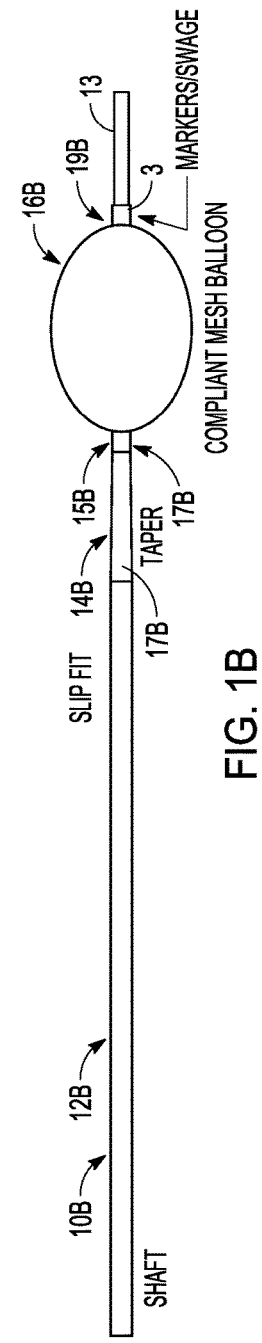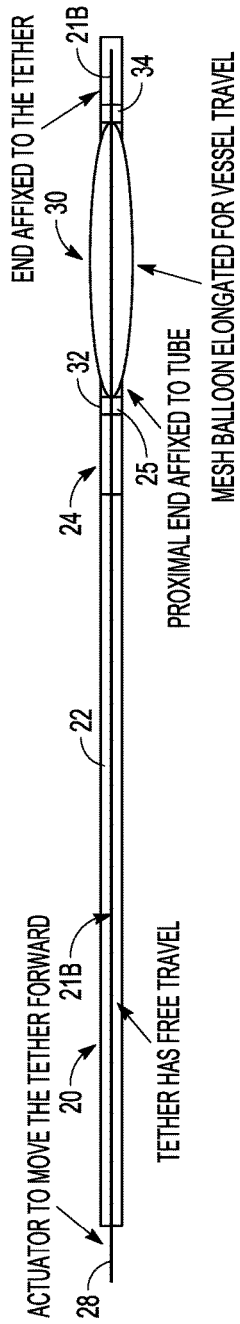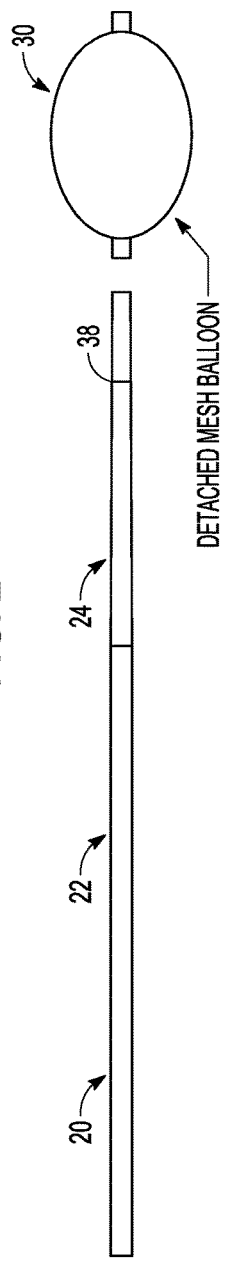

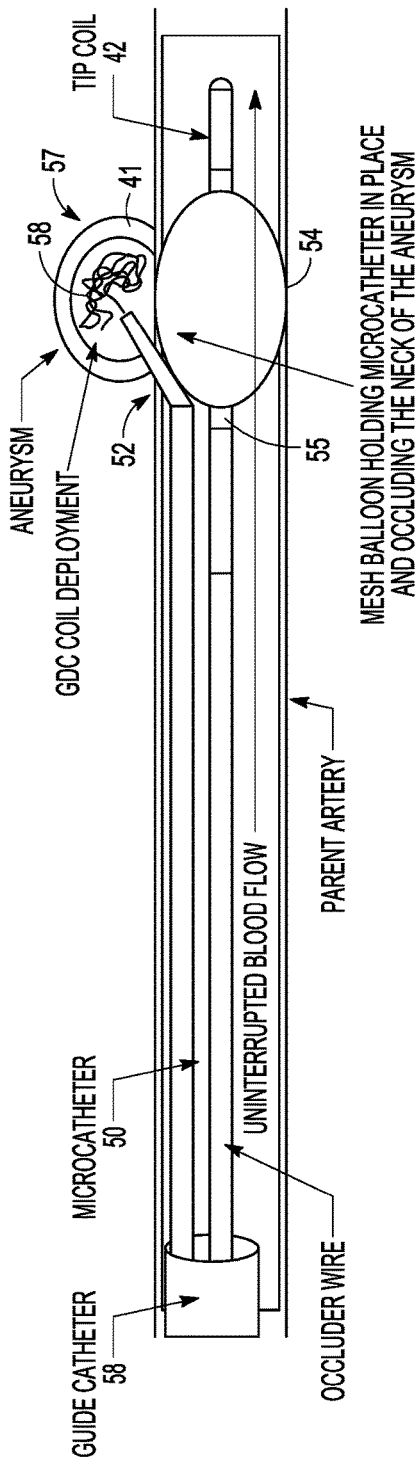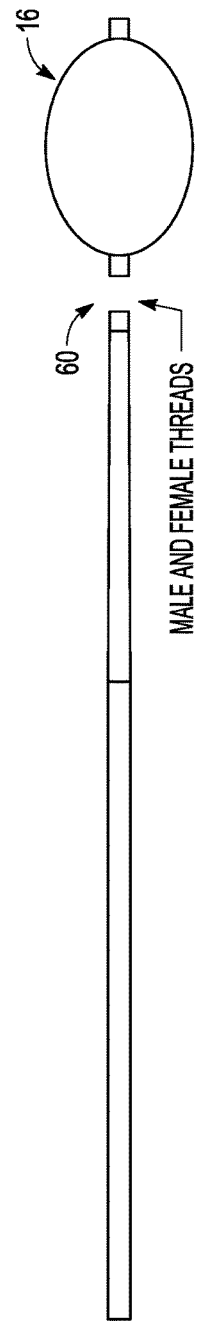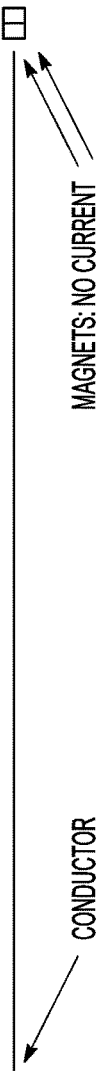
FIG. 4
FIG. 5
FIG. 5B

MAGNETS CURRENT TO WIRE MAGNET

MAGNETIC POLARITY COULD BE CHANGED IN THE WIRE MAGNET ELECTRICALLY OR MECHANICALLY. IF A CURRENT IS APPLIED

MAGNETS IN PROPER ORIENTATION

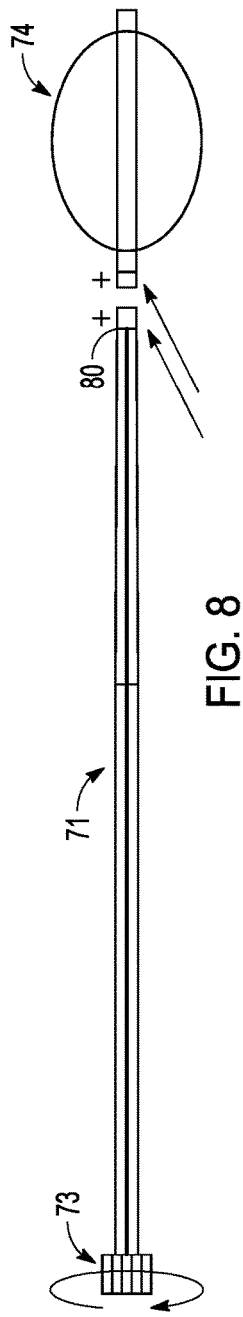
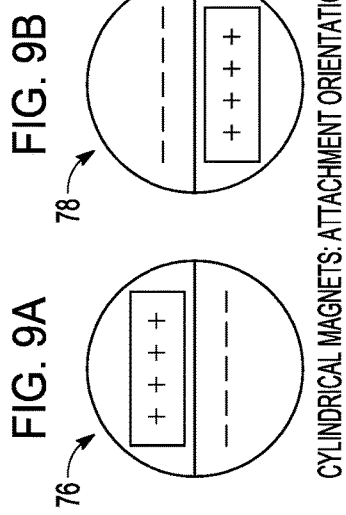
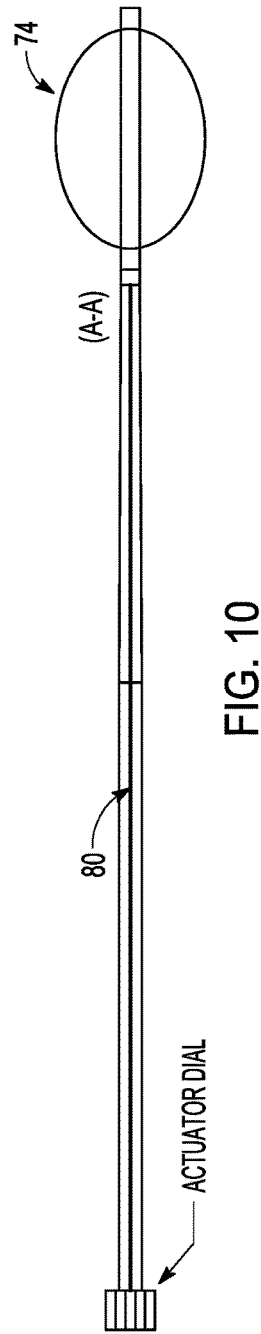

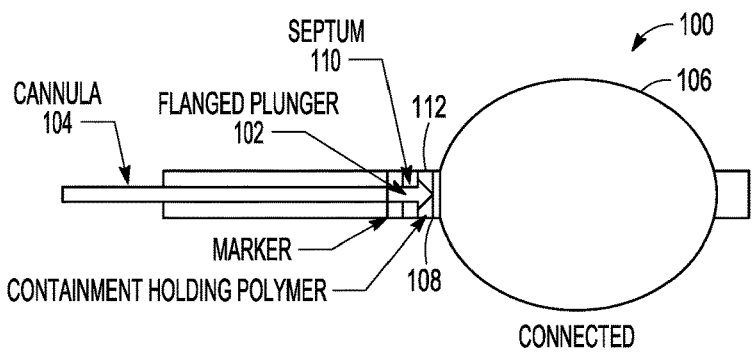
FIG. 10A (A-A)
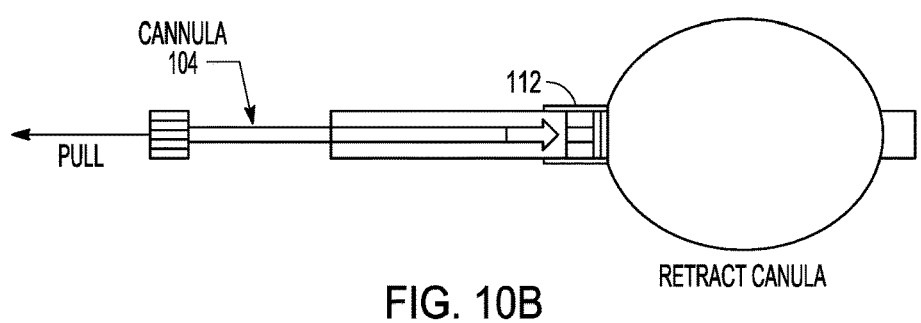
FIG. 10B
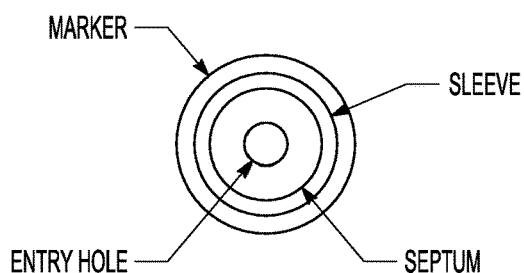
FIG. 10C (B-B)
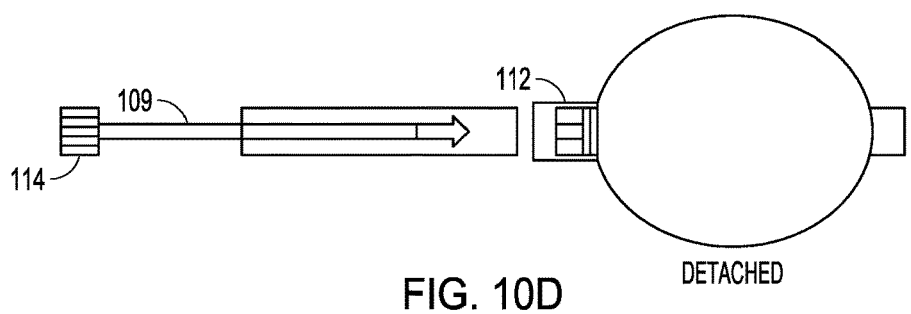
FIG. 10D

GUIDEWIRE/ PARTIAL OCCLUDER FOR INTRALUMINAL TRAVEL

CLAIM OF PRIORITY

This application is a U.S. National Stage filing under 35 U.S.C. § 371 from International Patent Application Serial No. PCT/US2014/022730, filed Mar. 10, 2014, published on Oct. 9, 2014 as WO 2014/164535, which claims the benefit of priority of U.S. Provisional Patent Application Ser. No. 61/776,492, filed on Mar. 11, 2013, the benefit of priority of which is claimed hereby, and which is incorporated by reference herein in its entirety.

FIELD OF THE INVENTION

Inventive embodiments disclosed herein relate to a guidewire/partial occluder for intraluminal travel within the human vasculature for the purpose of temporarily or permanently blocking the opening of a physiologic lumen, vessel branch, aneurysm neck and the like.

BACKGROUND

The prior art includes methods for occluding vessel openings. However, the methods are catheter based and employ a very thin wall compliant balloon on a distal tip of the catheter to achieve occlusion. These devices also require the use of a guidewire to track to a desired location. In addition, because of the thin wall, when the distal balloon is inflated with contrast media, the balloon is susceptible to rupture as well as being susceptible to rupture in use.

SUMMARY

Inventive subject matter disclosed herein includes a device that includes a hollow tube having a tapered distal end, sized to fit within a blood vessel. The device also includes a tether positioned within the hollow tube and an actuator effective for moving the tether forward and backward with respect to the hollow tube. The device also includes a compliant mesh balloon having a proximal end and a distal end, wherein the proximal end is attached to the hollow tube and the distal end is affixed to the tether wherein forward movement of the tether by movement of the actuator elongates the mesh balloon for travel through the blood vessel.

Another inventive embodiment includes a device comprising: A solid wire having a tapered distal end, sized to fit within a blood vessel; A coil affixed to the tapered distal end of the solid wire; A compliant mesh balloon having a proximal end and a distal end, wherein the proximal end is attached to the solid wire and the distal end is affixed to the coil, wherein forward movement of the coil elongates the mesh balloon for travel through the blood vessel.

Another inventive embodiment includes a device comprising: A tube having a telescoped distal end comprising tube portions that slip fit with respect to each other, sized to fit within a blood vessel; An actuator effective for moving the telescoped slip fit forward and backward with respect to the tube; and A compliant mesh balloon having a proximal end and a distal end, wherein the proximal end is attached to the tube and the distal end is affixed to the telescoped slip fit wherein forward movement of the telescoped slip fit by movement of the actuator elongates the mesh balloon for travel through the blood vessel.

DESCRIPTION OF THE DRAWINGS

FIG. 1a illustrates one side view embodiment of the flexible wire device with a solid wire and a mesh fixed balloon and a distal coil.

FIG. 1b illustrates a side view of the flexible wire device of FIG. 1 with the mesh fixed balloon positioned on a wire taper.

FIG. 2 illustrates a side view of a device with a hollow wire and mesh balloon in a collapsed position.

FIG. 3 illustrates a side view of the mesh balloon of FIG. 1 or FIG. 2 in a detached position.

FIG. 4 illustrates a longitudinal cross-sectional view of the device of FIGS. 1a or 1b within a blood vessel adjacent to an occlusion.

FIG. 5 illustrates a side view of the mesh balloon of FIG. 1a, FIG. 1b FIG. 2 and FIG. 4 wherein the balloon is detached by reversing a threaded connection between the distal end of the wire and the proximal end of the mesh balloon.

FIG. 5b illustrates a separation of the balloon from the wire.

FIG. 8 illustrates a longitudinal cross-sectional view of the device with mesh balloon of FIG. 7A or FIG. 7B wherein the magnet tipped canula extends the length of the proximal wire body and has an actuator which allows the user to rotate the magnet tipped canula and change the polarity of the canula magnet, thus again attaining separation.

FIGS. 9A, 9B, 9C and 9D illustrate orientations of the magnets of FIGS. 7A, 7B, and FIG. 8. FIGS. 9A and 9B show the magnets in an attachment orientation. FIGS. 9C and 9D illustrate the magnets in a detachment orientation. The magnet tipped canula of FIGS. 7A, 7B and FIG. 8 extends the length of the proximal wire body and has an actuator which allows the user to rotate the magnet tipped canula and change the polarity of the canula magnet, from that shown in FIGS. 9A and 9B to that of FIGS. 9C and 9D, thus again attaining separation.

FIG. 10 illustrates a longitudinal cross-sectional view of another embodiment of the flexible wire device.

FIG. 10A illustrates a cross-sectional view of a detachment mechanism of the flexible wire device embodiment of FIG. 10.

FIG. 10B illustrates a cross-sectional view of the flexible wire device of FIG. 10 wherein the cannula is retracted.

FIG. 10C illustrates a radial cross section of the flexible wire device of FIG. 10.

FIG. 10D illustrates the flexible wire device of FIG. 10 wherein the mesh balloon is detached.

DETAILED DESCRIPTION

Figure 6:
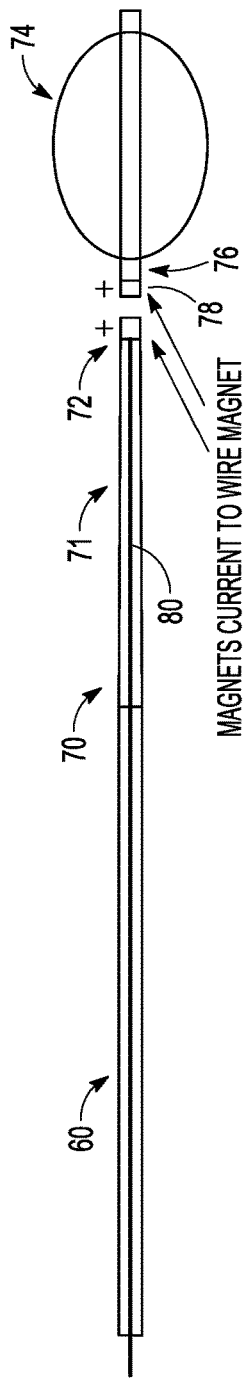
FIG. 6 illustrates a side view of the mesh balloon detachable by incorporation of two small magnets in the proximal end of the mesh balloon and the distal mating end of the guidewire

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In accordance with inventive embodiments disclosed herein, the guidewire/partial occluder is intended for, but not limited to introduction and partial occlusion within the vessels of the heart, brain, hepatics, lumbar, pancreatic and the like. The invention embodiments include a wire body having a proximal end and a distal end and a distal mesh balloon affixed to the distal end of the wire body. Radiopaque markers are placed on either end of the mesh balloon for the purpose of providing radiopacity as well as to act as a swage which holds the mesh balloon in place on the wire shaft.

Inventive subject matter disclosed herein includes a device that includes a hollow tube having a tapered distal end, sized to fit within a blood vessel. The device also includes a tether positioned within the hollow tube and an actuator effective for moving the tether forward and backward with respect to the hollow tube. The device also includes a compliant mesh balloon having a proximal end and a distal end, wherein the proximal end is attached to the hollow tube and the distal end is affixed to the tether wherein forward movement of the tether by movement of the actuator elongates the mesh balloon for travel through the blood vessel.

The inventive embodiments disclosed herein relate to a wire shown at 10a in FIG. 1a, 10b in FIG. 1b for a solid wire embodiment and 22 in FIG. 2 for a hollow wire embodiment that are useful for temporary or permanent vascular occlusion within the coronary, thoracic and peripheral and neurovasculature of the human body. Depending on the wire diameter selected, these occlusion wire embodiments are well suited for distal deployment and for providing partial occlusion of the vessels within the heart, brain, hepatics, lumbar, pancreatic vessels and the like. The wire embodiments 10a 10b and 22 include a mesh balloon, such as shown at 16 in FIGS. 1a and 16b in FIG. 1b and 30 in FIG. 2, attached to a distal end of the wire 10a, 10b *a* or 22, that is made such that selected sections of the mesh wire are treated so as to impede flow of blood or other bodily fluids where desired, either completely or partially, slowing the velocity of the fluid if desired.

For some embodiments, a layer of lubricious material is bound to an outer surface of the wire 10a, 10b or 22 and mesh balloon 16, 16b or 30 for a distance of 65 cm to 100 cm for the purpose of tracking the wire within a guiding catheter such as is shown at 59 in FIG. 4, within a vessel smoother and less traumatic.

Yet another aspect of the inventive embodiment is the incorporation of a radiopaque or echogenic coating onto the wire shaft which enables device visualization within a fluoroscopic or ultrasound imaging system. The mesh balloon is fabricated with one or more of a variety of materials that include metals and polymers. In one embodiment, the mesh balloon is fabricated using superelastic or shape memory nitinol.

The inventive embodiment disclosed herein at 10a in FIG. 1a includes a device that includes a flexible solid wire 12 having a tapered distal end 14, sized to fit within a blood vessel. The device 10a also includes a compliant mesh balloon 16 having a proximal end 4 and a distal end 6, wherein the proximal end 4 is attached to the flexible solid wire 12 and the distal end 6 is affixed to a coil 17. Forward movement of the coil 17 elongates the mesh balloon 16 and reduces the diameter of the mesh balloon for travel through the blood vessel.

Another inventive embodiment, illustrated at 10b in FIG. 1b includes a device that has a tube 12b having a telescoped distal end 14b that includes one or more tubular portions 20b that slip fit with respect to each other. The tube and tube portions are sized to fit within a vessel, such as a blood vessel. A distal mesh balloon 16b includes a proximal end 15b affixed to a tube portion of the slip fit and a distal portion 19b affixed to a distal tip 13 of the device 10b. The location of the mesh balloon 16b and distal tip 13 are determined with one or more markers 3.

Another device embodiment 20, shown in FIG. 2, includes a hollow wire 22 that encloses a tether 21b. Attached to the hollow wire 22 at its distal end is a mesh balloon 30. The device also includes an actuator 28 effective for moving telescoped slip fit tubular portion 24 forward and backward with respect to the hollow wire 22. The mesh balloon 30 includes a proximal end 32 and a distal end 34, wherein the distal end is attached to the tube 24 and the proximal end is affixed to the telescoped slip fit tubular portions wherein forward movement of the telescoped slip fit tubular portions by movement of the actuator elongates the mesh balloon 30 for travel through the blood vessel.

The flexible wire device 20 in FIG. 2 is constructed using a tandem slip-fit tube combination 24 wherein a proximal end 32 of the mesh balloon 30 is affixed to a distal end 25 of the larger outer tube 24 and the distal end 34 of the balloon 30 to the smaller inner tube tether 21b which extends within the lumen of the inner tube 24 and allows for reducing the diameter of the mesh balloon 30 by axially advancing the tether 2 lb forward in order to reduce the diameter of the mesh balloon 30 and facilitate vascular travel without the need for a catheter. See FIG. 2.

The flexible solid wire 12 and 12 and flexible hollow wire embodiments 12b and 22 are sized and shaped for navigating through more tortuous locations within the human vasculature for the treatment of various disorders by Interventionalists. Said wire embodiments 12, 12b and 22 have an outer diameter ranging from 0.010 inches (0.25 mm) to 0.038 inches (0.95 mm). The distal end of the wire embodiments 12, 12b and 22 is tapered to allow for improved tracking characteristics. The taper embodiments 14, 14b and 24 have a length that is in a range from approximately 8 inches to 14 inches. The distal wire diameter at the tip of the taper embodiments 14, 14b and 24 depend on the initial wire diameter. However, the diameter ranges from 0.002 inches to 0.010 inches.

In addition, a compliant occluder (also referred to as the mesh Balloon) embodiments 16, 16b and 30 are affixed to the distal end of the wire embodiments 12, 12b and 22 on the taper embodiments 14, 14b, and 24. The occluder embodiments are designed to block the opening to a lumen in the vasculature as shown for one embodiment in FIG. 4, yet allow blood to flow through the mesh balloon, unlike some balloon occluder devices currently on the market which stop blood flow. The occluder embodiments 16, 16b and 30 are braided, laser cut, woven or made by any other method known in the art. Materials for fabrication may include but are not limited to metal wire, both flat and round, metal tubing, polymeric filaments as well as polymeric tubing.

The inventive embodiments disclosed herein employ a solid wire or a hollow wire which is composed of Nitinol, Titanium, Stainless steel or other suitable metal. Conversely, the wire may also be fabricated from a suitable polymer as well. Marker bands, one example of which is shown at 38 in FIG. 3, are included on either end of the occluder 30. These marker bands are used by a physician to gauge distance between the proximal and distal ends of the occluder.

For some embodiments, a platinum wire or other radiopaque material is formed into a coil and placed over the distal end of the wire, from an occluder 41 to the tip, wherein the tip is finished with a bead to reduce the potential for trauma to the vessel, as shown at 42 in FIG. 3. For some embodiments, a lubricious coating is applied over a distance of 65 cm-100 cm from the distal tip of the wire. Said lubricious coating aids in the tracking of the wire through the vasculature. The purpose of the distal occluder 41 is to provide support during delivery of a device or agent.

The compliant mesh balloon (also called "occluder") embodiments 16, 16b or 30 employed in embodiments disclosed herein are self-expanding and can be reduced in diameter by insertion into a luminal shaft such as a catheter as shown in FIG. 4 or the wire body of the mesh balloon can be mechanically elongated thereby reducing the outer diameter of the mesh balloon, such as is shown in FIGS. 1a, 1b, and 2. The mesh balloon embodiments can be fabricated with a variety of materials that include both metals and polymers. In one embodiment, the mesh balloon is fabricated using superelastic or shape memory nitinol. The mesh balloon may be fabricated into a variety of shapes such as round, elliptical, elongated and special shapes which are formed by heat setting the mesh material on a mandrel. The mesh balloon is fabricated with one or more of a variety of materials that include metals and polymers. In one embodiment, the mesh balloon is fabricated using superelastic or shape memory nitinol.

Inventive embodiments disclosed herein employ a wire of metal or polymer as the main body of the device. An occluder is affixed to the distal end of the device. The occluder is designed such that it is compliant so as to be able to compress into a lumen for tracking and delivery. In addition, radiopaque markers are placed on either end of the occluder for visualization under imaging techniques and also to affix the mesh balloon to the shaft of the device. A lubricous coating is applied to the device for the purpose of aiding wire movement during tracking and placement.

The device embodiments disclosed herein can be used in conjunction with a catheter or tracked by themselves in the vasculature, as shown at 50 in FIG. 4. The tube or wire embodiments such as 12, 12b, 22 disclosed herein have use as a guidewire. The body of the guidewire is, for some embodiments, comprised of a metal tube or wire or appropriate polymeric material. A compliant mesh balloon 54 attached to a distal wire shaft taper 55 enables the user to block an aneurysm neck or the like with said mesh balloon 54 in order to anchor a catheter 56 within a vessel and aid in the deployment of coils 58 or other such devices as shown at 56 in FIG. 4.

The mesh balloon 54 in FIG. 4, is, for some embodiments, fabricated from an appropriate metal or extruded polymer. The mesh balloon is braided, knitted, laser cut, etched or coiled to fabricate the desired shape. The mesh balloon is, for some embodiments, heat shaped on an appropriate mandrel to achieve a variety of configurations which are also self-expanding. A shape memory material such as nitinal can be employed in the fabrication of the mesh balloon, for some embodiments, as well, in order to take advantage of varied shapes at certain temperatures. This may aid in proper deployment.

Another unique feature of all of the device embodiments disclosed herein is the ability of the mesh balloon to allow for blood flow through the mesh balloon and parent artery during placement, unlike conventional occlusion balloons, which are not mesh and which block the parent artery off completely when inflated as shown in FIG. 4.

The mesh balloon, also called the occluder, for all embodiments is self-expanding and the radial force applied to the vessel wall is adjustable based on the selected materials' physical properties as well as the dimension of the material being used.

In one embodiment, the mesh balloon, such as 16, 16b, or 30 or 54 is detached from the tip of the wire for the purpose of permanently occluding a vessel, fistula, aneurysm and the like as shown for one embodiment, at 60 in FIG. 5. Detachment is achieved by inductive heating for some embodiments or mechanical separation methods for other embodiments.

The detached mesh balloon is, for some embodiments, placed over the neck of an aneurysm or other vascular deformity, and, given its round to spherical shape, reduces the risk of blocking perforators emptying into the parent artery.

The occluder 16, 16b or 30 or 54 is, for some embodiments, selectively open to flow by webbing a portion of the balloon with an appropriate dispersion thereby impeding flow in that segment of the mesh balloon. The webbing is made to be radiopaque so as to further improve visualization and placement.

In one embodiment, the mechanism for detachment is achieved using inductive heat to release the mesh balloon. For this embodiment, an area of detachment is made of a material having a lower melting point than the other portion of the wire or tube. In yet another embodiment, the balloon is detached by reversing a threaded connection between the distal end of the wire and the proximal end of the mesh balloon. See FIG. 5b.

In another embodiment illustrated at 60 in FIG. 6, wherein a cannula 71 includes a tip magnet 72, a mesh balloon 74 is detached by incorporation of two small magnets 76 and 78 in the proximal end of the mesh balloon 74 and the distal mating end of the guidewire 80. Said magnets 76 and 78 are encapsulated in a biocompatible material to ensure biocompatibility and stability.

Figure 7A:
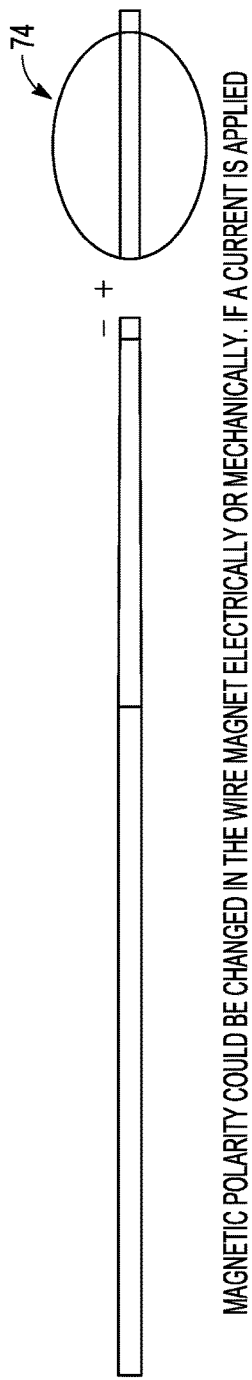
FIG. 7A illustrates a side view of a device embodiment with a mesh balloon detachable by incorporation of two small magnets in the proximal end of the mesh balloon and the distal mating end of the guidewire.
Figure 7B:
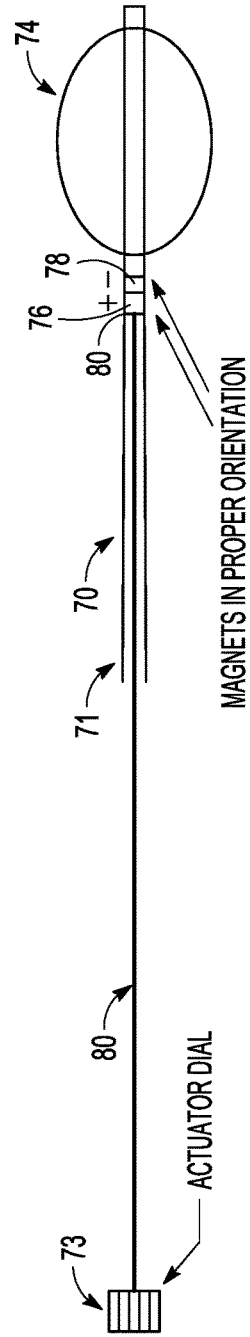
FIG. 7B illustrates a cross-sectional view of the device embodiment of FIG. 7A with the detachable mesh balloon of FIG. 7A with magnets oriented in a position that retains the mesh balloon

Detachment occurs by changing the polarity on the wire side magnet, resulting in the wire and magnet having the same polarity and repulsion, thus separation of the mesh balloon 74 to the wire side magnet, as shown in FIGS. 6 and 7A and 7B. The polarity is altered to match the mesh balloon side magnet, thus aiding in separation. Magnetic polarity is changed by using the magnet tipped cannula 71 which extends the length of the proximal wire body and which includes an actuator 73 which allows the user to rotate the magnet tipped cannula and change the polarity of the cannula magnet 72, thus again attaining separation. See FIG. 8 and FIGS. 9A and 9B, which show the magnets attachment orientation and FIGS. 9C and 9D which show the magnets detachment orientation. When the cannula 71 is rotated 180° so that polarity is matched, separation of the mesh balloon occurs. Rotational direction of actuator dial 73 is made clockwise or counter-clockwise for other embodiments, to rotate the cannula and separate the mesh balloon.

Another detachment device includes a mechanical approach to detaching the mesh balloon from the wire body. This approach, illustrated at 100 in FIG. 10 A includes a flanged plunger 102 fixed to a cannula 104 which is inserted into containment on an occluder 106 proximal end 108. Within the containment is a septum 110 fabricated of an appropriate material which, when the flanged plunger 102 is inserted into it, the connection 112 holds securely. Detachment occurs when the cannula 104 is advanced forward until it engages the containment housing 112. The cannula movement, controlled by an actuator dial 114 is then unlocked and drawn proximally until the flanged plunger 102 is clear of the septum 110, as shown in FIG. 10B. The septum 110 material is biocompatible and yet mechanically suitable for the system, such as a cured silicone or other appropriate material. See FIGS. 10A and 10B.

In another embodiment, the flanged septum is bonded, with an appropriate material, within the marker and is removed by drawing back on the tether cannula thereby releasing the wire/tether from the mesh balloon. Detachment is achieved by withdrawing the retainer tube while buttressing the coil marker with the cannula tube.

It should be noted that these detachment systems disclosed herein are usable for a variety of devices where detachment of a coil, stent and the like are required.

The embodiments are described in sufficient detail to enable those skilled in the art to practice the invention. Other embodiments may be utilized and formulation and method of using changes may be made without departing from the scope of the invention. The detailed description is not to be taken in a limiting sense, and the scope of the invention is defined only by the appended claims, along with the full scope of equivalents to which such claims are entitled.

It will be appreciated by those skilled in the art that changes could be made to the embodiments described above without departing from the broad inventive concept thereof It is understood, therefore, that this invention is not limited to the particular embodiments disclosed, but it is intended to cover modifications within the spirit and scope of the present invention as defined by the present description.

What is claimed is:

1. A device comprising:
   a hollow tube having a tapered distal end, sized to fit within a vessel of a living being;
   a tether positioned within the hollow tube;
   an actuator effective for moving the tether forward and backward with respect to the hollow tube;
   a compliant mesh balloon having a proximal end and a distal end, wherein the proximal end is attached to the hollow tube and the distal end is affixed to the tether wherein forward movement of the tether by movement of the actuator elongates the mesh balloon for travel through the vessel of a living being, and
   a detaching mechanism for detaching the compliant mesh balloon from the device, the detaching mechanism comprising, a proximal magnetic component, attached at a proximal end of the mesh balloon and a distal magnetic component defining a positive portion having a positive polarity and an opposing negative portion having a negative polarity, attached to the tether, wherein the magnetic components are encapsulated in a biocompatible material and contact each other when the mesh balloon is attached to the device;
   the detaching mechanism further comprising a cannula with a tip to which a cannula magnetic component is attached, the cannula magnetic component having a positive portion having a positive polarity and an opposing negative portion having a negative polarity, wherein rotation of the cannula magnetic component proximal to the distal magnetic component moves the negative portion and positive portion of the distal magnetic component and changes polarity of the distal magnet, producing repulsion of the distal magnetic component for the proximal magnetic component, separating the mesh balloon from the device.

2. The device of claim 1, wherein the compliant mesh balloon is comprised of a metal.

3. The device of claim 2, wherein the metal is nitinol.

4. The device of claim 1, further comprising another actuator positioned at a proximal end of the hollow tube, the actuator in communication with the tether.

5. The device of claim 1, further comprising a microcatheter, wherein the device is insertable in the microcatheter.

6. The device of claim 1, deployed in a catheter.

* * * * *